(12) United States Patent
Smith

(10) Patent No.: US 7,205,695 B2
(45) Date of Patent: Apr. 17, 2007

(54) HIGH SPEED ROTOR

(75) Inventor: James S Smith, Old Lyme, CT (US)

(73) Assignee: DRS Power & Control Technologies, Inc., Milwaukee, WI (US)

( * ) Notice: Subject to any disclaimer, the term of this patent is extended or adjusted under 35 U.S.C. 154(b) by 0 days.

(21) Appl. No.: 10/867,489

(22) Filed: Jun. 14, 2004

(65) Prior Publication Data

US 2004/0245884 A1 Dec. 9, 2004

Related U.S. Application Data

(60) Continuation of application No. 10/408,331, filed on Apr. 7, 2003, now Pat. No. 6,750,584, which is a division of application No. 09/063,362, filed on Apr. 21, 1998, now Pat. No. 6,000,288.

(51) Int. Cl.
*H02K 1/18* (2006.01)

(52) U.S. Cl. .................. 310/218; 310/217; 310/156.38

(58) Field of Classification Search ........... 310/156.38, 310/156.48–49, 156.51–54, 156.55–59, 156.61–69, 310/156.71, 261–263, 265, 216–218
See application file for complete search history.

(56) References Cited

U.S. PATENT DOCUMENTS

| | | | | |
|---|---|---|---|---|
| 3,979,821 A | * | 9/1976 | Noodleman | 29/598 |
| 4,588,914 A | * | 5/1986 | Heyne | 310/156.11 |
| RE33,655 E | * | 8/1991 | Hershberger | 68/23.7 |
| 5,140,211 A | * | 8/1992 | Ucida | 310/156.61 |
| 5,889,346 A | * | 3/1999 | Uchida et al. | 310/156.57 |

FOREIGN PATENT DOCUMENTS

EP 0333871 9/1989

* cited by examiner

*Primary Examiner*—Thanh Lam
(74) *Attorney, Agent, or Firm*—Sonnenschein Nath & Rosenthal LLP

(57) ABSTRACT

An electromagnetic machine is provided. The machine includes a stator extending along a longitudinal axis and having an inner surface defining a rotor receipt cavity. The rotor extends along and is rotatable about the longitudinal axis within the rotor receipt cavity. A plurality of ring assemblies are supported on the rotor and a plurality of magnets are circumferentially spaced about the rotor and extend through the ring assembly. Each magnet is generally parallel to the axis of the rotor.

3 Claims, 5 Drawing Sheets

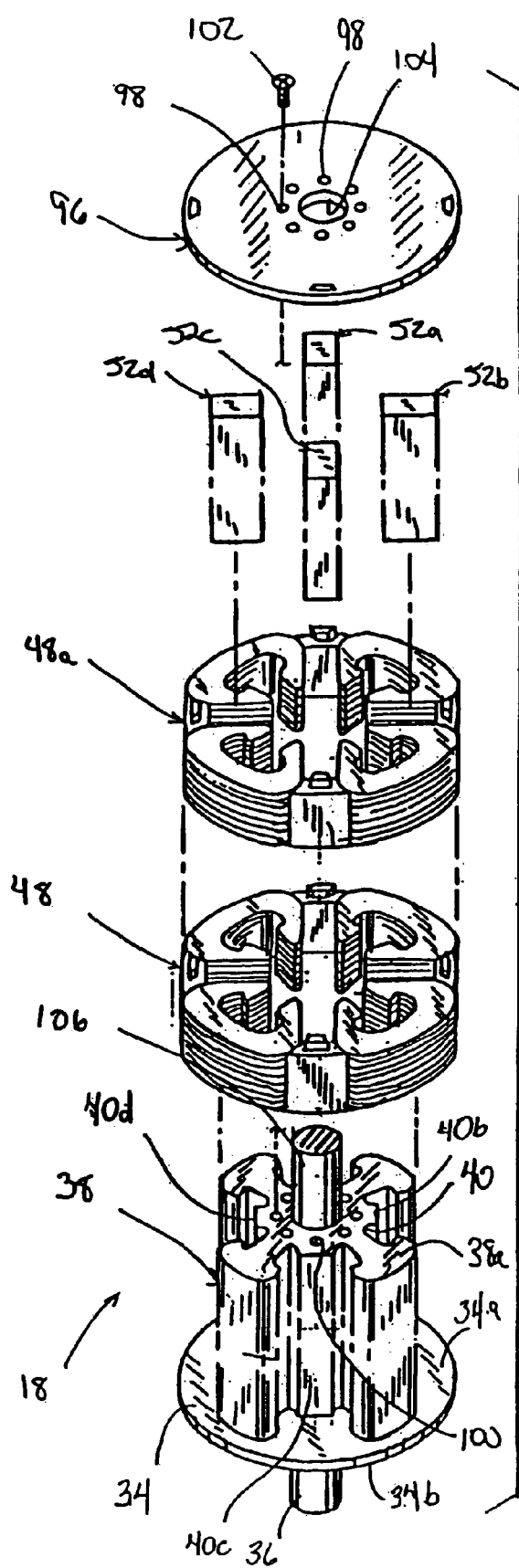
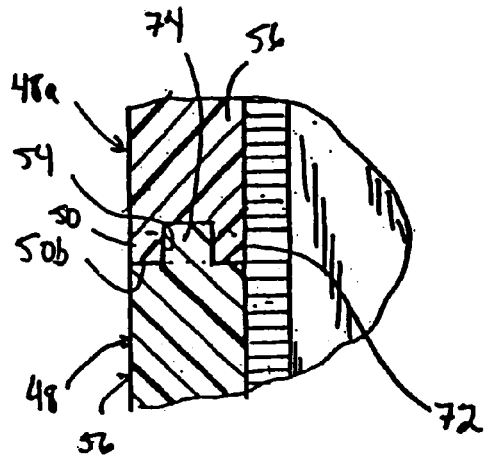
FIG.5
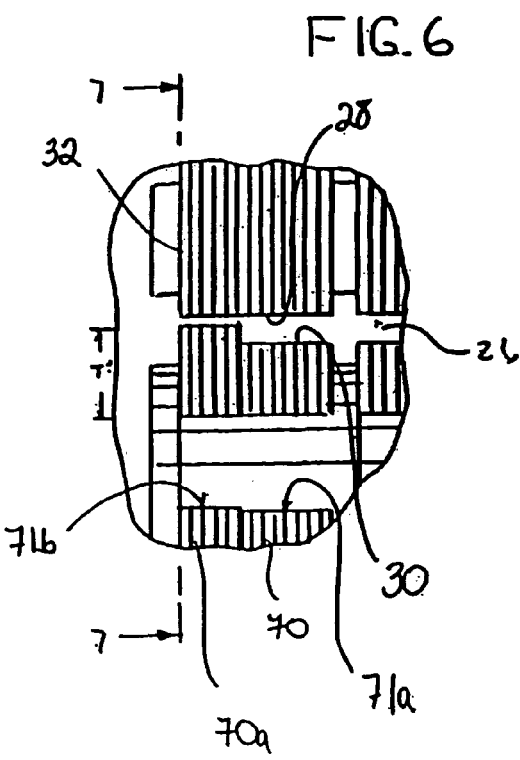
FIG.6
FIG.2

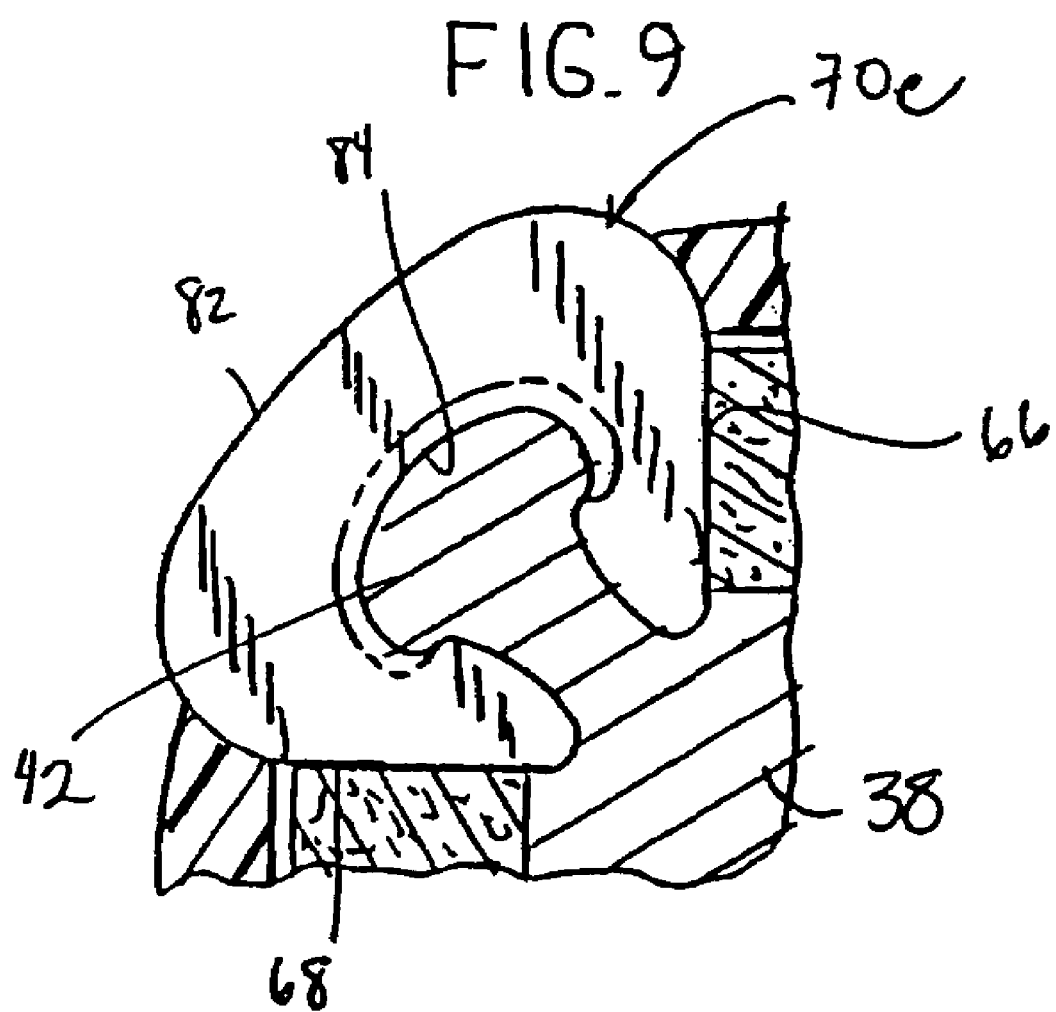

HIGH SPEED ROTOR

The present application is a continuation application of U.S. patent application Ser. No. 10/408,331 filed Apr. 7, 2003, now U.S. Pat. No. 6,750,584 which is a divisional application of U.S. patent application Ser. No. 09/063,362 filed Apr. 21, 1998, now U.S. Pat. No. 6,750,584, which issued on Jun. 15, 2004 the disclosure of which is incorporated herein by reference.

FIELD OF THE INVENTION

This invention relates to electromechanical machines, and in particular, to a permanent magnet electromechanical machine incorporating a high speed rotor design.

BACKGROUND AND SUMMARY OF THE INVENTION

In order to meet the constant demand for efficient, power dense drivers for industrial and commercial applications, high speed, permanent magnet electric motors and generators are required. Presently, however, there are very few permanent magnet electric motors or generators that are rated over several hundred kilowatts (kW) and that provide high speed shaft rotation. While shaft speeds of up to approximately 100,000 revolutions per minute (rpm) have been achieved in permanent magnet electric motors and generators having low power ratings, higher rated machines are typically limited to shaft speeds of several thousand rpms or less. In order to provide high speed, permanent magnet electric motors and generators, a rotor designed for high speed rotation is required.

Permanent magnet electric motors and generators typically incorporate a drum-shaped rotor having permanent magnets located thereon to establish magnetic poles. In a first rotor construction, the permanent magnets are fastened on the outer surface of the rotor drum. This type of rotor construction is known as a "surface mounted" permanent magnet rotor. Alternatively, the permanent magnets may be embedded below the surface of the motor. This type of rotor construction is known as an "embedded" permanent magnet rotor. Both types of rotor constructions utilize rare earth magnets. As is known, rare earth magnets typically have poorer mechanical properties than the other elements of the rotor, and as such, cannot be used as load bearing elements in the rotor design. Further, rare earth magnets exhibit a weak resistance to corrosion, as well as, to the flow of electricity. Consequently, rare earth magnets can be demagnetized by exposure to corrosive environments or high temperatures caused by eddy currents flowing in the magnets, or any other heat generating mechanism of the machine's operation.

Surface mounted permanent magnet rotors are conceptually simple, and therefore, perceived to be less costly. Typically, the magnets are retained on the outer diameter of the rotor in one of four ways. First, the magnets may be enclosed in a non-ferromagnetic holder that is attached to the rotor by mechanical means such as fasteners, a version of "tongue and groove" geometry, or a combination of both. Second, the magnets may be glued directly to the outer surface of the rotor. Third, the magnets may be glued directly to the outer surface of the rotor, and thereafter, a non-ferromagnetic, metal sleeve is shrink-wrapped around the magnets. Fourth, the magnets may be glued directly to the outer surface of the rotor, and thereafter, the rotor assembly is wrapped with a high strength, high modulus composite fiber/epoxy.

Each of the prior designs for surface mounted permanent magnet rotors has certain shortcomings. For example, in the designs wherein the magnets are shielded by a metallic sleeve, the metallic sleeve is subjected to higher order harmonics in the stator due to the power supply and the stator slot geometry. As a result, eddy currents are generated in the metallic sleeve so as to cause heating of the rotor and the magnets. At very high frequencies, such as those experienced in machines running significantly faster than approximately 3600 rpms, the heating of the metallic sleeve can damage the magnets. As such, rotor thermal management is a significant design consideration for any high speed, permanent electric motor or generator using such a magnet retention means.

In the designs wherein the magnets are glued to the rotor or wherein a composite fiber/epoxy wraps is used to retain the magnets on the rotor, the electrical properties of the magnetic material allow eddy currents to flow, thereby heating the magnets directly. It can be appreciated that a composite wrap over the magnets makes the cooling of the magnets a greater challenge since the composite wrap also acts to thermally insulate the magnets. Alternatively, simply gluing the magnets to the rotor is not feasible for high speed applications as the mechanical properties of the magnets are not up to the task of holding together when subjected to the tensile loads that results from high rotational speeds. Further, finding a suitable adhesive for gluing the magnets on the rotor may be difficult.

An additional drawback to surface mounted permanent magnet rotors is the cost of the magnets. The surface mounted magnets are necessarily shaped to closely fit the outer surface of the rotor. Shaping the surface mounted magnets involves the precision grinding of each magnet at its interface with the rotor, usually before magnetization, followed by the use of special tooling to energize the magnets after they are installed on the rotor. These manufacturing steps can add significantly to the overall cost of the final product. Finally, surface mounted rotors are more susceptible to damaging the magnets in "off-design" operating conditions, such as pole slips or stator short circuits.

While rotors that incorporate magnets embedded below the surface of the rotor are more complex in appearance, this type of rotor constructions has proved to be relatively simple to design, manufacture and assemble. In such embedded magnet rotor configuration, the rotor is made of a non-ferromagnetic material and the magnets are arranged so that the direction of magnetization is perpendicular to an axial point passing through the middle of each installed magnet and the rotor center line. Laminated pole pieces are installed on the sides of each magnet, with the polarity of the magnets arranged to have the same polarity on each side of a particular pole piece. As a result, a magnetic pole is formed on the outside diameter of the rotor. The embedded magnet rotor configuration has the advantage of shielding the magnets from the stator harmonics that can cause eddy current heating in the magnets, as well as, damage to the magnets from the high flux transients and reversals resulting from stator short circuits or pole slipping during operation. In addition, the laminated pole pieces effectively limit eddy currents in the poles, and thus, the heating of the rotor in total. Further, in embedded magnet rotor configurations, the magnets are usually simple rectangular shapes and are installed magnetized. As a result, a manufacturer does not have to invest in unique magnetizing tooling for each rotor diameter being produced. This, in turn, significantly reduces the cost of the final product. In view of the foregoing, it can be appreciated that the embedded magnet rotor configuration offers greater design freedom since the burden of cooling the rotor is limited and/or eliminated.

Heretofore, in embedded magnet rotor configurations, the magnets are restrained from movement in the radial direction by the pole pieces. For example, wedges or other blocking features may be used to restrain radial movement of the magnets. These wedges or blocking features are attached to the rotor by keyed tangs, "fir-tree" tongue and groove geometry and composite fiber/epoxy materials wound around the outside diameter, or any combination of the above. Alternatively, the magnets may have a trapezoidal cross section with the pole pieces being in contact with the magnets. If the magnets move radially away from the rotor center, the magnets and the pole pieces are loaded in compression by their respective geometries. In most circumstances, these arrangements for embedding the magnets within the rotor are adequate. However, the mechanical properties of the magnet materials and pole pieces limit the surface speeds such machines can achieve, making them most suitable for low RPM, high torque/power design.

Therefore, it is a primary object and feature of the present invention to provide a rotor assembly for use in high speed, permanent magnet electric motors and/or generators that maximizes protection for the magnets thereof in cases of stator short circuits and pole slips during operation.

It is a further object and feature of the present invention to provide a rotor assembly for use in high speed, permanent magnet electric motors and/or generators that have higher power ratings than prior permanent magnet electric motors and/or generators.

It is a further object and feature of the present invention to provide a rotor assembly for use in high speed, permanent magnet electric motors and/or generators which is simpler and less expensive to manufacture than prior permanent magnet rotors.

In accordance with the present invention, a rotor assembly is provided for an electromechanical machine. The rotor assembly includes a rotor connectable to a shaft for rotational and movement therewith. The rotor extends along an axis and has first and second circumferentially spaced lobes projecting radially therefrom. First and second sets of laminated pole pieces are provided. Each set of laminated pole pieces is receivable on a corresponding lobe. A magnet is disposed between the sets of pole pieces.

The rotor assembly includes a magnet retention ring for preventing radial movement of the magnet. The magnet retention ring has a radially outer edge and includes a backing plate and a magnet retention element. The backing plate has first and second cutouts therein for receiving corresponding lobes therethrough. The magnet retention element projects from a first side of the backing plate and extends between the first and second sets of laminated pole pieces. Each lobe projecting from the rotor includes a neck terminating at an enlarged head. Each laminated pole piece is generally c-shaped and includes first and second ends separated by a predetermined distance for accommodating the neck of a corresponding lobe therebetween. The magnet retention element includes a radially outer surface extending between the first and second sets of laminated pole pieces and an inner surface directed towards the magnet. A shim may be positioned between the inner surface of the magnet retention element and the magnet for preventing radial movement of the magnet during rotation of the rotor.

Each set of laminated pole pieces includes a plurality of first pole pieces having a first radial thickness and a plurality of second pole pieces having a second radial thickness. The plurality of first pole pieces of a corresponding set of laminated pole pieces are positioned adjacent each other to form a first stack and the plurality of second pole pieces of the corresponding set of laminated pole pieces are positioned adjacent each other to form a second stack. It is contemplated that the first radial thickness be greater than the second radial thickness to control end leakage of flux.

In accordance with a further aspect of the present invention, a rotor assembly is provided for an electromechanical machine. The rotor assembly includes a rotor connectable to a shaft for rotational movement therewith. The rotor extends along an axis and has a plurality of circumstantially spaced lobes projecting radially therefrom. A plurality of ring assemblies are supported on the rotor. Each ring assembly includes a plurality of circumferentially spaced poles supported on corresponding lobes. A plurality of magnets are circumferentially spaced about the rotor and extend through the ring assemblies. Each magnet is generally parallel to the axis of the rotor and is disposed between corresponding pairs of poles of each ring assembly.

Each ring assembly includes a magnet retension ring for preventing radial movement of the plurality of magnets. Each magnet retention ring has a radially outer edge and includes a backing plate and a plurality of circumferentially spaced magnet retention elements projecting from a first side of the backing plate. The backing plate has a plurality of cutouts therein for receiving corresponding lobes therethrough. It is contemplated that each magnet retention element extends between corresponding pairs of poles and has a retaining bar projecting from the terminal thereof. Each backing plate includes a second side having a plurality of circumferentially spaced retaining bar receipt cavities formed therein. Each retaining bar receipt cavity is adapted for receiving a corresponding retaining bar of an adjacent magnet retention ring in a mating relationship.

Each of the poles of each ring assembly includes a plurality of laminated pole pieces. The rotor includes first and second ends wherein one of the plurality of ring assemblies is positioned adjacent the first end of the rotor. The laminated pole pieces of each of the poles of the one of the plurality of ring assemblies positioned adjacent the first end of the rotor includes a plurality of first pole pieces having a first radial thickness and a plurality of second pole pieces having a second radial thickness. The first radial thickness of the first pole pieces is greater than the second radial thickness of the second pole pieces and are positioned adjacent the first end of the rotor. It is contemplated that all of the laminated pole pieces include a generally arcuate, radially outer edge. In addition, all of the laminated pole pieces include a leading edge and a trailing edge which are asymmetrical.

In accordance with a still further aspect of the present invention, an electromagnetic machine is provided. The machine includes a stator extending along a longitudinal axis and having an inner surface defining a rotor receipt cavity. A rotor is positioned within the rotor receipt cavity. The rotor extends along and is rotatable about the longitudinal axis. A plurality of ring assemblies are supported on the rotor. Each ring assembly includes a plurality of circumferentially spaced poles. A plurality of magnets are circumferentially spaced about the rotor and extend through the ring assemblies. Each magnet is generally parallel to the axis of the rotor and is disposed between corresponding pairs of poles of each ring assembly.

The rotor of the electromagnetic machine includes a plurality of circumferentially spaced lobes projecting radially therefrom. Each ring assembly includes a plurality of circumferentially spaced poles supported on corresponding lobes. Each of the poles of each ring assembly includes a plurality of laminated pole pieces. The rotor includes first and second ends and one of the plurality of ring assemblies is positioned adjacent the first end of the rotor. The laminated pole pieces of each of the poles of the one of the plurality of ring assemblies positioned adjacent the first end of the rotor includes a plurality of first pole pieces having a first radial thickness and a plurality of second pole pieces having a second radial thickness. It is contemplated that the first radial thickness of the first pole piece be greater than the second radial thickness of the second pole pieces. The first pole pieces are positioned adjacent the first end of the rotor. Each laminated pole pieces includes a leading edge and a trailing edge which are asymmetrical.

The stator of the electromagnetic machine includes a plurality of laminated stator pieces laminated along an axis generally parallel to the longitudinal axis. The laminated stator pieces are radially spaced from the poles of the rotor assemblies. The stator may include a plurality of radially extending cooling channels extending therethrough. The cooling channels communicate with the rotor receipt cavity in order to cool the rotor.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

FIG. 2 is an exploded, isometric view of the rotor assembly of the present invention;

FIG. 5 is a cross-sectional view of the rotor assembly of the present invention taken along line 5—5 of FIG. 4;

FIG. 6 is an enlarged, cross-sectional view showing a portion of the electromechanical machine of FIG. 1;

FIG. 9 is an enlarged, cross-sectional view of a portion of the rotor assembly of FIG. 4 showing the second alternate embodiment of the pole pieces for the rotor assembly.

DETAILED DESCRIPTION OF THE INVENTION

Figure 1:
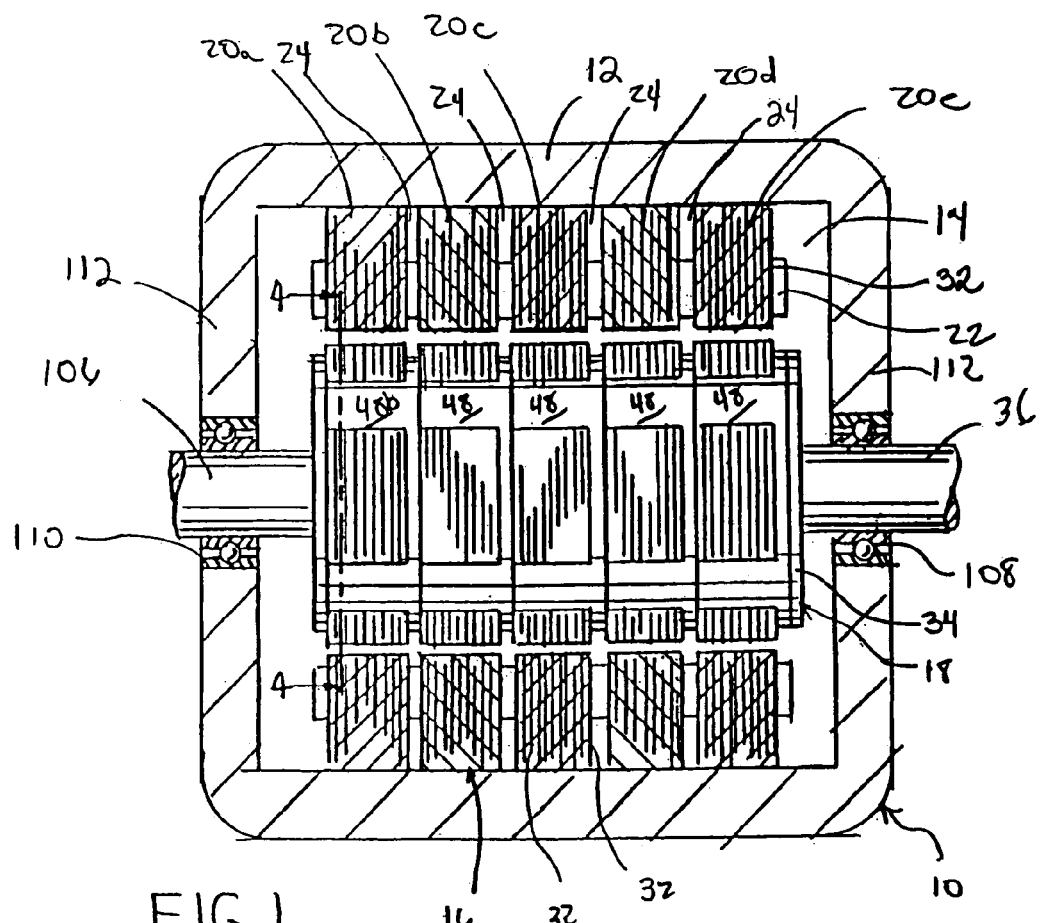
FIG. 1 is a cross-sectional view of an electromechanical machine incorporating a rotor assembly in accordance with the present invention.

Referring to FIG. 1, an electromechanical machine incorporating a rotor assembly 15 in accordance with the present invention is generally designated by the reference numeral 10. Electromechanical machine 10 includes an enclosure 12 which defines an interior 14 for receiving stator 16 and rotor assembly 18, as hereinafter described. Stator 16 includes a plurality of stator stacks 20a–20e which are positioned adjacent each other and supported by stator frame 22. Radial cooling channels 24 extend between corresponding pairs of stator stacks 20a–20e so as to allow air or an alternate coolant to pass therethrough into air gap 26 defined between the radially inner surfaces 28 of stator stacks 20a–20e and radially outer surface 30 of rotor assembly 18, FIG. 6. As best seen in FIGS. 1 and 6, stator stacks 20a–20e are formed by a plurality of stator pole pieces 32 laminated together.

Figure 3:
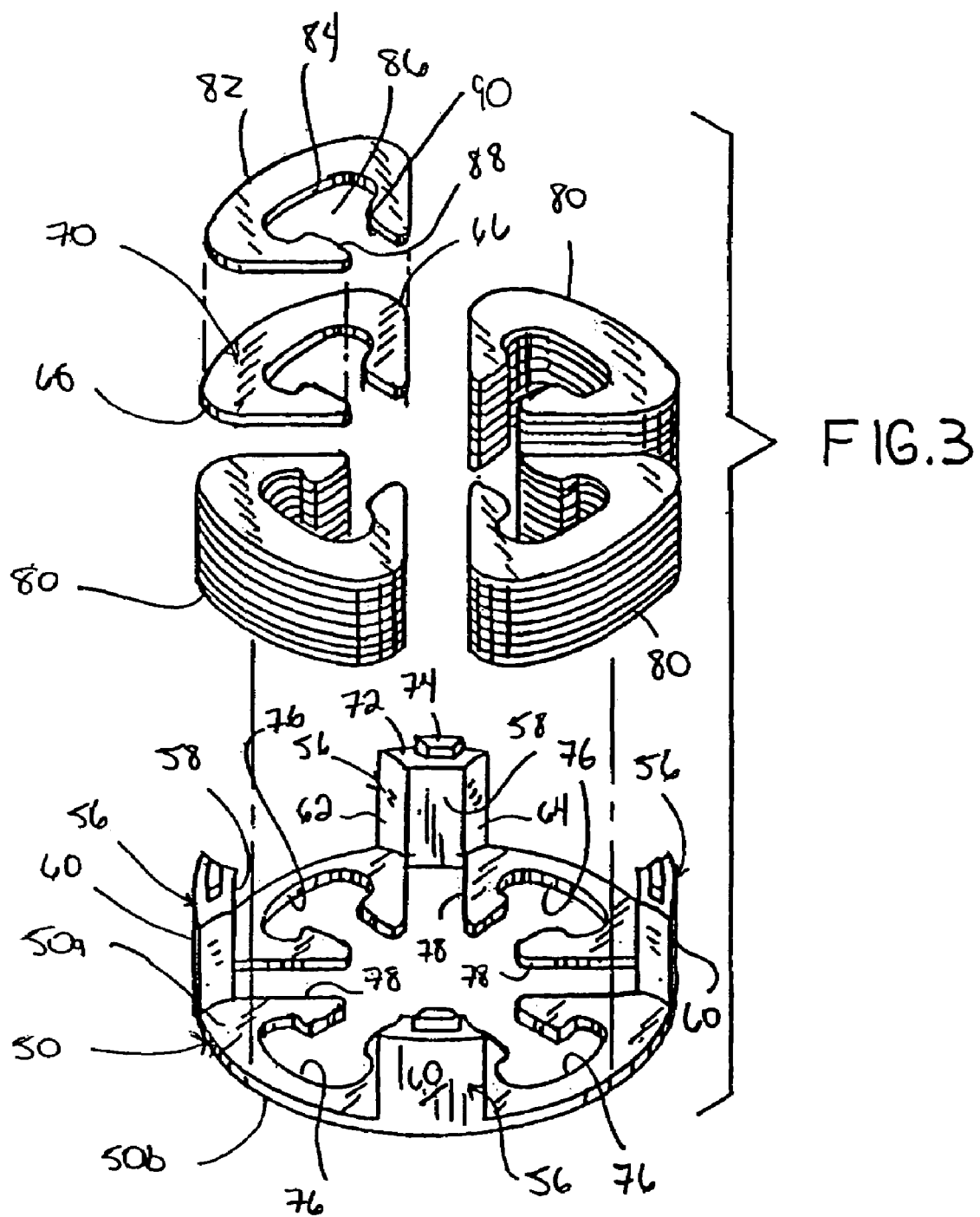
FIG. 3 is an exploded, isometric view of the ring assembly for the rotor assembly of the present invention.
Figure 7:
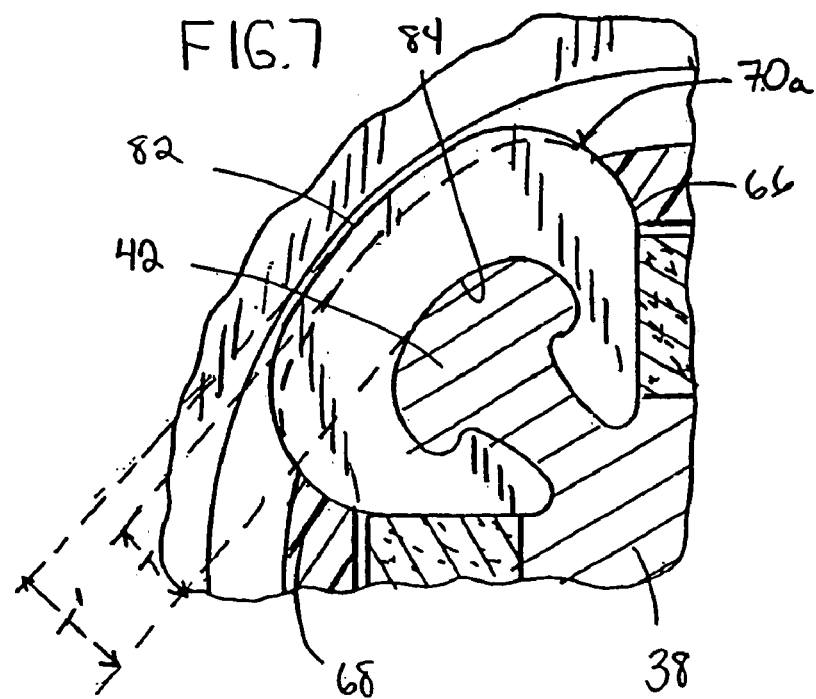
FIG. 7 is a cross-sectional view of the electromechanical machine taken along line 7—7 of FIG. 6.

Referring to FIGS. 2–3, rotor assembly 18 includes an end plate 34 having first and second opposite sides 34a and 34b, respectively. A rotatable stub shaft 36 is operatively connected to second side 34b of end plate 34 in any conventional manner so as to translate rotation of shaft 36 to end plate 34. Rotor 38 extends from first side 34a of end plate 34 and is operatively connected thereto in any conventional manner. It is contemplated to form rotor 38 from various types of materials including magnetic, ferromagnetic, non-ferromagnetic, and high strength materials. However, it can be appreciated that rotor 38 may be formed of other materials without deviating from the scope of the present invention.

Figure 4:
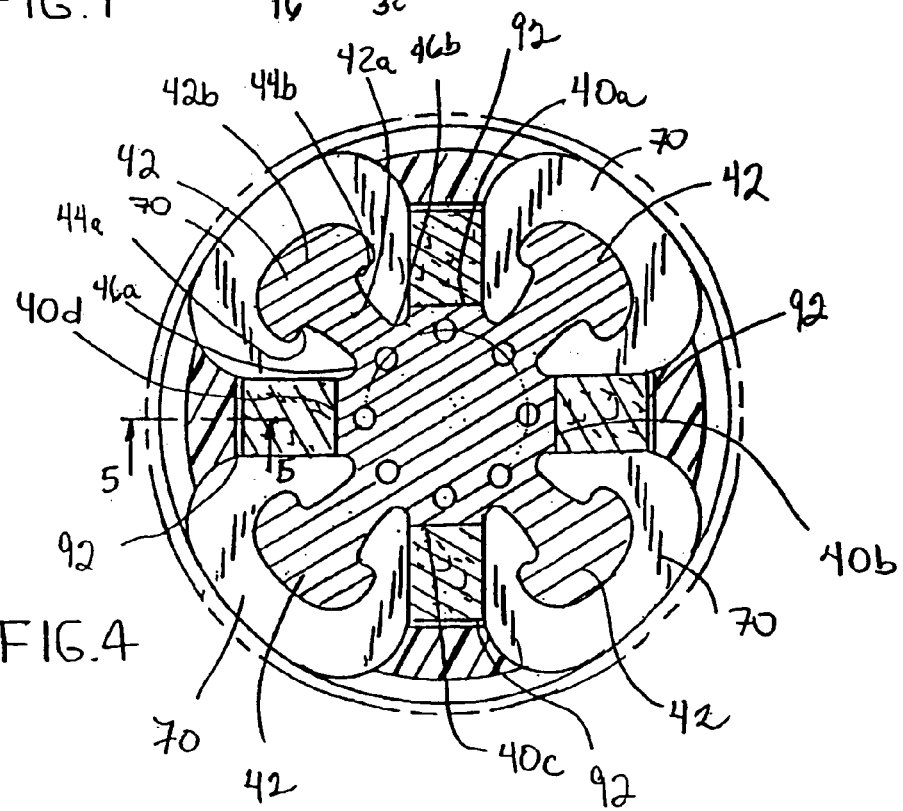
FIG. 4 is a cross-sectional view of a rotor assembly of the present invention taken along line 4—4 of FIG. 1.

Rotor 38 is generally cylindrical in shape and includes a radially outer surface 40 defining a plurality of circumferentially spaced, flat lands 40a–40d, FIG. 4. A plurality of circumferentially spaced lobes 42 extend from radially outer surface 40 of rotor 38 between corresponding pairs of lands 40a–40d. Each lobe 42 includes neck portion 42a extending from outer surface 40 of rotor 38 and an enlarged head 42b on the terminal end of neck portion 42a. It is contemplated to round the intersections 44a and 44b of enlarged head 42b and neck 42a of each lobes 42 in order to avoid stress at such intersections 44a and 44b during operation of electromechanical machine 10. Similarly, the intersections 46a and 46b of neck portion 42a of each lobe 42 and radially outer surface 40 of rotor 38 are rounded so as to reduce stress at such intersection 46a and 46b during operation of electromechanical machine 10. The number and locations of such intersections may be increased and distributed along the radial interface of the lobe 42 and the laminated pole pieces, 70, described hereinafter.

Rotor assembly 18 further includes a plurality of ring assemblies 48 supported on rotor 38. Referring to FIG. 3, each ring assembly 48 includes a magnet retention ring 50 for preventing radial movement of magnets 52a–52d, as hereinafter described. Each magnet retention ring 50 includes first and second opposite sides 50a and 50b, respectively. A plurality of circumferentially spaced retaining bar receipt cavities 54, FIG. 5, are provided in second side 50b of magnet, for reasons hereinafter described.

A plurality of circumferentially spaced magnet retention elements 56 project from first side 50a of magnet retention ring 50. Each magnet retention element 56 includes a generally, flat radially inner surface 58 and a generally arcuate radially outer surface 60. Inner surface 58 and outer surface 60 of magnet retention element 56 are separated by first and second generally arcuate sides 62 and 64, respectively. Sides 62 and 64 of each magnet retention element 56 are shaped to form a mating relationship with the leading and trailing edges 66 and 68, respectively, of corresponding laminated pole pieces 70, as hereinafter described.

Each magnet retention element 56 terminates at a generally flat terminal end surface 72. Retaining bar 74 projects axially from end surface 72 of each magnet retention element 56. Each retaining bar 74 is axially aligned with a corresponding retaining bar receipt cavity 54 formed in second side 50b of magnet retention ring 50 such that retaining bar 74 may be axially received within a corresponding retaining bar receipt cavity 54 formed in second side of magnet retention ring 50 of an adjacent ring assembly 48a, FIGS. 2 and 5, so as to interlock adjacent ring assemblies 48 and 48a.

Magnet retention ring 50 further includes a plurality of circumferentially spaced lobe-shaped cutouts 76 which are dimensioned to allow magnet retention ring 50 to be slid axially onto lobes 42 of rotor 38. In addition, magnet retention ring 50 includes a plurality of circumferentially spaced magnet cutouts 78 therein for allowing corresponding magnets 52a–52d to pass therethrough, as hereinafter described.

Ring assemblies 48 further include a plurality of stacks 80 of a predetermined number of laminated pole pieces 70. Each laminated pole piece 70 (and hence, each stack 80 of laminated pole pieces) is generally c-shaped and has an arcuate, radially outer edge 82 and inner edge 84 which defines a lobe-shaped gap 86 therethrough for allowing each stack 80 of laminated pole pieces 70 to be received on a corresponding lobe 42. Each laminated pole piece 70 terminates at first and second end 88 and 90, respectively, which are separated by a predetermined distance to accommodate neck portion 42a of a corresponding lobe 42 therebetween. This feature is intended to retain the pole pieces in position during operation and therefore, may be altered to include as many lobed lands along the radial interface between the laminated pole pieces 70 and the rotor lobe 42.

Stacks 80 of laminated pole pieces 70 are positioned on first sides 50a of magnet retention ring 50 to form ring assemblies 48. When stacks 80 of laminated pole pieces 70 are positioned, leading edges 66 of laminated pole pieces 70 engage first sides 62 of corresponding magnet retention elements 56 and trailing edges 68 of laminated pole pieces 70 engage second sides 64 of corresponding magnet retention elements 56. In addition, lobe-shaped gaps 86 defined by the laminated pole pieces 70 are axially aligned with a corresponding lobe-shaped cutouts 76 in magnet retention ring 50 of corresponding ring assemblies 48.

As best seen in FIGS. 1 and 2, rotor assembly 18 is constructed by axially sliding ring assemblies 48 onto rotor 38 such that lobes 42 of rotor 38 extend through a corresponding lobe-shaped cutouts 76 in magnet retention ring 50 and gaps 86 defined by laminated pole pieces 70 of corresponding stacks 80 of ring assemblies 48. Retaining bars 74 projecting from end surfaces 72 of magnet retention elements 56 are seated within corresponding retaining bar receipt cavities 54 in second sides 50b of magnet retention ring 50 of adjacent ring assemblies 48a, FIGS. 2 and 5, as heretofore described, in order to interlock adjacent ring assemblies 48. Magnets 52a–52d are slid axially along corresponding lands 40a–40d of outer surface 40 of rotor 38 such that magnets 52a–52d extend through corresponding magnet cutouts 78 in ring assemblies 48 and such that magnets 52a–52d are disposed between corresponding pairs of stacks 80 of laminated pole pieces 70 in ring assemblies 48. It is contemplated to provide shims 92 between magnets 52a–52b and radially inner surfaces 58 of corresponding magnet retention elements 56 of each ring assembly 48 so as to prevent radial movement of magnets 52a–52d during the rotation of rotor assembly 18, and thermal growth of the rotor 18 as the machine warms during operation.

After ring assemblies 48 and magnets 52a–52d are assembled on rotor 38, second end plate 96 is secured to terminal end 38a of rotor 38 to maintain ring assemblies 48 and magnets 52a–52d thereon. Second end plate 96 includes a plurality of circumferentially spaced bolt openings 98 which are axially aligned with corresponding bolt receipt apertures 100 formed in terminal end 38a of rotor 38. Bolts 102 extend through corresponding openings 98 in second end plate 96 and into bolt receipt apertures 100 in terminal end 38a of rotor 38 so as to interconnect second end plate 96 to rotor 38. Second end plate 96 includes a central aperture 104 for allowing stub shaft 106, operatively connected to terminal end 38a of rotor 38 in any conventional manner, to pass therethrough. As best seen in FIG. 1, stub shafts 36 and 106 pass through corresponding bearings 108 and 110, respectively, in sidewalls 112 and 114, respectively, of enclosure 12 so as to rotatably support rotor assembly 18. In its assembled condition, it can be appreciated that electromechanical machine 10 may be utilized as an electric motor or a generator.

Referring to FIGS. 1 and 6, in order to limit the end leakage of the magnet flux provided by permanent magnets 52a–52d during operation of electromechanical machine 10, it is contemplated to reduce the reluctance of the radial flux path across air gap 26. This is accomplished by forming stacks 80 of ring assembly 48b adjacent terminal end 38a of rotor 38 from a first set 71a of laminated pole pieces 70 having a radial thickness T and a second set 71b of laminated pole pieces 70a having a thickness T'. Except for the radial thickness, laminated pole pieces 70a are identical in structure to laminated pole pieces 70, and as such, the prior description of laminated pole pieces 70 can be understood to describe laminated pole pieces 70a, as if it is fully described herein.

Figure 8:
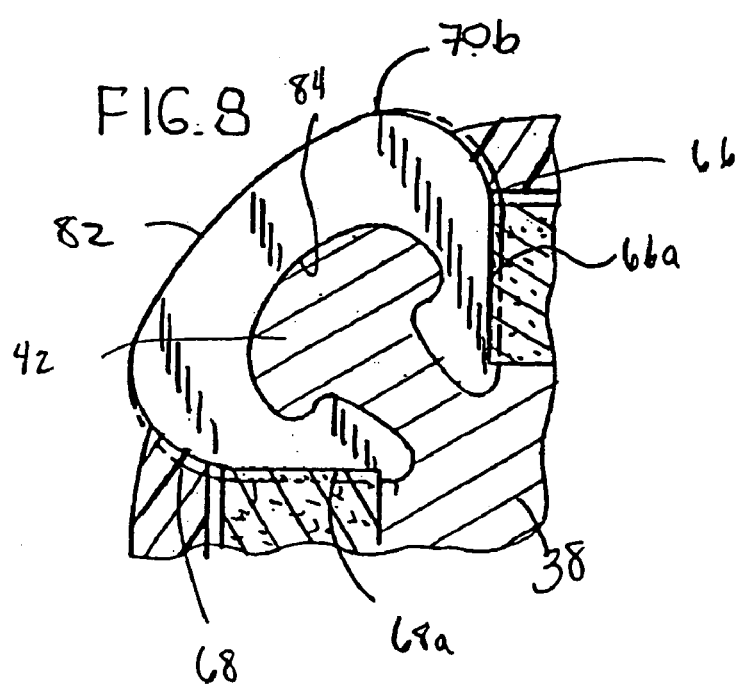
FIG. 8 is an enlarged, cross-sectional view of a portion of the rotor assembly of FIG. 4 showing an alternate embodiment of the pole pieces for the rotor assembly of the present invention.

Referring to FIGS. 8 and 9, additional alternate laminated pole pieces 70a may be provided adjacent terminal end 38a of rotor 38. By way of example, referring to FIG. 9, it is contemplated to shape inner edge 84 of laminated pole pieces 70a to the outer surface of a corresponding lobe 42 so as to help control the face flux distribution under various operating loads of electromechanical machine 10. Alternatively, referring to FIG. 8, it is contemplated to provide recesses 68a and 68b in the leading and trailing edges 66 and 68, respectively, of laminated pole pieces 70a.

Various modes of carrying out the invention are contemplated as being within the scope of the following claims particularly pointing out and distinctly claiming the subject matter which is regarded as the invention.

I claim:

1. A rotor assembly for an electromechanical machine, comprising:
   a rotor;
   a plurality of stacks of laminated pole pieces, the stacks being circumferentially disposed about said rotor;
   a plurality of magnets wherein a respective one of said magnets is disposed between a respective adjacent pair of said stacks of laminated pole pieces;
   a first means for retaining each of said magnets between each adjacent pair of said stacks of laminated pole pieces; and
   a second means for retaining each of said stacks of laminated pole pieces on said rotor, wherein the first means does not include any of the pole pieces and is not a part of the second means,
   whereupon rotational movement of said rotor, said magnets are prevented from moving radially by said first means without mechanical interaction between the first means and the stacks of laminated pole pieces, and said stacks of laminated pole pieces are prevented from moving radially by said second means.

2. A rotor assembly of claim 1, wherein the first means comprises a magnet retention ring axially aligned with said plurality of stacks of laminated pole pieces, said magnet retention ring having a first side and a plurality of circumferentially spaced magnet retention elements projecting from the first side, each magnet retention element being disposed between one adjacent pair of said stacks of laminated pole pieces.

3. A rotor assembly of claim 1, wherein the rotor comprises an outer surface and a plurality of lobes extending from the outer surface and circumferentially spaced about a central axis of the rotor, each lobe being adapted to removably engage and retain one or more of the laminated pole pieces of a respective stack on said rotor, and wherein the second means includes the plurality of lobes.

* * * * *